United States Patent [19]

De Heij

[11] 4,346,045
[45] Aug. 24, 1982

[54] PROCESS FOR RESOLVING DL-S-BENZOYL-β-MERCAPTOISOBUTYRIC ACID, AND PRODUCTS OBTAINED

[75] Inventor: Nicolaas A. De Heij, Venlo, Netherlands

[73] Assignee: Océ-Andeno B.V., Venlo, Netherlands

[21] Appl. No.: 239,899

[22] Filed: Mar. 3, 1981

[30] Foreign Application Priority Data

Mar. 6, 1980 [NL] Netherlands .................. 8001341

[51] Int. Cl.$^3$ ............................................ C07C 153/07
[52] U.S. Cl. ............................... 260/455 R; 562/401
[58] Field of Search ................ 260/455 R; 562/401

[56] References Cited

U.S. PATENT DOCUMENTS 3,879,451  4/1975  Yoshioka et al. ............... 562/401
4,224,457  9/1980  Iwao et al. ....................... 562/401

OTHER PUBLICATIONS

H. Kaehler et al.-Liebigs Annalen der Chemie 757 (1972), pp. 15–22 at 17, 19 and 21.

*Primary Examiner*—Natalie Trousof
*Assistant Examiner*—Vera C. Clarke
*Attorney, Agent, or Firm*—Albert C. Johnston

[57] ABSTRACT

Resolution of DL-S-benzoyl-β-mercaptoisobutyric acid into its optical antipodes is effected by treating the DL-acid in solution with D-(+)-N-benzyl-α-phenethylamine. The D(−)-S-benzoyl-β-mercaptoisobutyric acid itself as well as its salts, esters or derivatives can be obtained advantageously by this process.

4 Claims, No Drawings

PROCESS FOR RESOLVING DL-S-BENZOYL-β-MERCAPTOISOBUTYRIC ACID, AND PRODUCTS OBTAINED

This invention relates to a process for resolving DL-S-benzoyl-β-mercaptoisobutyric acid and to D(—)-S-benzoyl-β-mercaptoisobutyric acid itself and its salts, esters or derivatives as obtained by use of the process.

DL-S-benzoyl-β-mercaptoisobutyric acid and its preparation are already known. The acid can be prepared, for example, by reacting thiobenzoic acid with methacrylic acid. It is also known that DL-S-benzoyl-β-mercaptoisobutryric acid can be resolved into its optical antipodes. For example, U.S. patent application Ser. No. 071,934, filed Sept. 4, 1979, describes a process for the preparation of optically active compounds of the formula

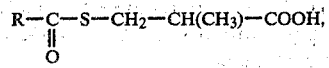

in which R can have one of the meanings indicated in that application. According to that disclosure the compounds can be prepared by resolving a compound of the above formula, in which R represents a phenyl group, by means of cinchonidine, D-(—)-2-aminobutanol-1 or a derivative of the latter and then, if so desired, re-acylating the product.

D (—)-S-benzoyl-β-mercaptoisobutyric acid is very suitable as a starting compound for the preparation of 1-(3-mercapto-2-D-methyl propanoyl)-L- proline and its derivatives. These proline compounds are biologically active and have interesting pharmaceutical properties, such as their lowering effect on certain forms of high blood pressure.

Although the resolving process described in the above-mentioned application is quite useful and gives reasonable yields, a need has remained, especially in view of the promising pharmaceutical properties of the above-mentioned proline compounds, for a process that will simplify the resolution of DL-S-benzoyl-β-mercaptoisobutyric acid and permit a higher yield, so a more economical production of the proline compounds.

The object of the present invention is to provide a process meeting this need.

It has been found that the object can be achieved by a process in which the resolution of DL-S-benzoyl-β-mercaptoisobutyric acid is carried out by means of D-(+)-N-benzyl-α-phenethylamine.

The latter compound (hereinafter referred to as NBPA) is known per se. According to the literature it can be prepared from optically active D-α-phenethylamine and benzyl chloride. It is not mentioned in S. H. Wilen's book: "Resolving agents and resolutions in organic chemistry" (1971), which is especially devoted to the subject of resolving agents and organic resolutions.

It has now been found that the resolution of DL-S-benzoyl-β-mercaptoisobutyric acid can be realized more simply and with a considerably higher yield with the use of NBPA than with the resolving process previously described. This is the case, in particular, when the resolution is carried out by the steps of:

(a) preparing a solution of DL-S-benzoyl-β-mercaptoisobutyric acid in isopropanol;

(b) adding to this solution NBPA as resolving agent, thus forming a salt of the NBPA with D-(—)-S-benzoyl-β-mercaptoisobutyric acid;

(c) crystallizing out and isolating the salt formed, and if required recrystallizing this salt to improve its optical purity;

(d) subjecting the pure salt to a basic hydrolysis process in order to remove the resolving agent, followed by acidifying the separated aqueous solution; and (e) isolating the liberated D-(—)-S-benzoyl-β-mercaptoisobutyric acid and, if required, purifying it.

Although solvents other than isopropanol, such as ethanol, n-butanol, toluene, acetone, ethyl acetate, t-butyl acetate and di-isopropyl ether can be used, the use of isopropanol is found more advantageous, so is preferred.

The invention is also directed of course to the products obtained by employing the present process. In this connection, the D-(—)-S-benzoyl-β-mercaptoisobutyric acid itself as well as its salts, esters or other derivatives are to be considered. Among such salts are, in addition to the NBPA-salt, the ammonium salts and alkaline (earth) metal salts such as the Na-, K-, Ca-, Ba-, and Mg-salts. Among such esters are simple esters such as the lower alkyl esters; and related simple compounds are contemplated among such derivatives.

The following examples further illustrate the practice of the invention.

EXAMPLE 1 a. Salification

A solution of 1 mol of DL-S-benzoyl-β-mercaptoisobutyric acid was prepared in 500 ml of isopropanol. To this solution 0.95 mol of NBPA was added. The resulting mixture was heated to about 45° C. After stirring the solution for half an hour at this temperature it was cooled, with stirring, to 20° C. After additional stirring for about 3 hours at that temperature, the crystallized salt was centrifuged, washed with approximately 50 ml of isopropanol and dried. The yield was 217 g, which corresponds to approximately 50%; melting point: 104°–106° C.

b. Recrystallisation of the salt

The 217 g of salt obtained above were added to 500 ml of isopropanol, after which the mixture was heated, with stirring, to approximately 70° C. At that temperature the salt dissolved completely. Stirring all the time, the solution was cooled slowly. Some seed crystals were added at 65° C., after which the solution was further cooled to 20° C. in about an hour's time and the stirring was prolonged at this temperature for approximately 2 hours.

The crystallized salt was centrifuged, washed with 50 ml of isopropanol and dried. The yield was 180 g (=approximately 41.5%); melting point: 107°–108° C. and $[\alpha]_D^{22} = -3°$ to $-4.4°$ (1% in 96% ethanol).

c. Liberation of the D(—)- isomer from the NBPA-salt

The 180 g of purified salt obtained by the process b were added to a stirred mixture of 200 ml of 1,2-dichloroethane, 53 g of soda and 500 ml of water. After vigorous stirring for one hour the dichloroethane layer was separated from the aqueous layer. The first layer contained the NBPA, the second the desired acid in the form of the sodium salt. With stirring, concentrated hydrochloric acid was added to the aqueous layer until a pH value of 1 was reached. The precipitated D-(−)-S-benzoyl-β-mercaptoisobutyric acid was filtered over a Büchner funnel, washed with water and dried. The overall yield was 40%; melting point: 67°–69° C. and $[\alpha]_D^{22} = -43°$ to $-44°$ (1% in 96% ethanol).

The greater part of the NBPA started from could be recovered from the various mother liquors. Moreover, the various isopropanol layers obtained during the working up process, which layers still contained remainders of the NBPA-salt of D-(−)-S-benzoyl-β-mercaptoisobutyric acid, can be reused.

Compared with the overall yield recorded in the above-mentioned patent application (22.4% in Example 1 and 30.7% in Example 2), the resolution according to the process of the present invention gives considerably higher yields.

Additional advantages of this process are that, generally, the reaction time is shorter and the number of purification steps smaller. Further, a strongly marked advantage lies in that the process can be carried out with considerably more concentrated solutions. Thus, while the amount of solvent required per one mol of DL-compound or resolving agent according to the examples of said patent application is 5,100 ml and 3,000 ml, respectively, an amount of 500 ml suffices according to the present invention.

Another advantage is that the resolution of the DL-S-benzoyl-β-mercaptoisobutyric acid can be carried out directly after its preparation from thiobenzoic acid and DL-methacrylic acid, i.e., without first isolating the DL-compound. This is not practicable, or scarcely is so, when the above-mentioned resolving agents other than NBPA are used. The following example 2 illustrates this manner of practicing the invention.

EXAMPLE 2

With stirring, 1.05 mol of thiobenzoic acid were added to 250 ml of isopropanol. The solution was heated to about 80° C. and 1.00 mol of methacrylic acid was added in about ½ hour's time. The resulting solution was heated to reflux temperature. After refluxing the solution for 2 hours it was cooled to 40° C., and 250 ml of isopropanol, 0.95 mol of NBPA and some seed crystals of the desired salt were added.

The mixture was stirred for ½ hour at 40° C. and was then cooled to 20° C., whereupon the stirring was continued for 4 hours at this temperature. The salt, which had meanwhile crystallized out, was centrifuged, washed with approximately 50 ml of isopropanol and dried. The yield was approximately 50%.

The salt obtained was further treated as described in Example 1 under b and c. The overall yield of D-(−)-S-benzoyl-β-mercaptoisobutyric acid was 39%; melting point: 67°–69° C.

Finally, the process making use of NBPA has the additional advantage that the NBPA can be recovered in a considerably simpler way than the resolving agents used heretofore. The recovery of the NBPA can be effected, for example, as follows:

The mother liquor of the resolving step is concentrated by evaporation, in which process the isopropanol is recovered. The residue is treated with 1,2-dichloroethane and diluted sodium hydroxide. After vigorous stirring for half an hour the dichloroethane layer is separated, washed with dilute sodium hydroxide and then twice with water. The dichloroethane layer is dried, the dichloroethane evaporated and the NBPA is recovered in a practically quantitative yield.

The mother liquor of the recrystallisation step can be reused for a next resolution or for crystallisation. From the dichloroethane layer liberated during the hydrolysis step the NBPA can be recovered quantitatively by washing the layer with diluted lye and water and evaporating the dichloroethane.

I claim:

1. A process for resolving DL-S-benzoyl-β-mercaptoisobutyric acid which comprises treating said acid in solution with D-(+)-N-benzyl-α-phenethylamine (NBPA), thus forming a salt of NBPA with D-(−)-S-benzoyl-β-mercaptoisobutyric acid, and isolating said salt.

2. A process according to claim 1, said DL-acid having been prepared by reaction of a solution of thiobenzoic acid with methacrylic acid, said treating being effected by adding the NBPA to a solution containing the products of said reaction.

3. A process according to claim 1 or 2 which comprises
   (a) preparing a solution of DL-S-benzoyl-β-mercaptoisobutyric acid in isopropanol;
   (b) adding to said solution D-(+)-N-benzyl-α-phenethylamine (NBPA) as resolving agent, thus forming a salt of the NBPA with D-(−)-S-benzoyl-β-mercaptoisobutyric acid;
   (c) crystallizing out and isolating said salt and if required recrystallizing it to improve optical purity;
   (d) subjecting the substantially pure salt to a basic hydrolysis to remove the resolving agent, followed by acidifying the separated aqueous solution; and
   (e) isolating the liberated D-(−)-S-benzoyl-β-mercaptoisobutyric acid from said aqueous solution and, if required, purifying it.

4. An isolated substantially pure salt of D(−)-S-benzoyl-β-mercaptoisobutyric acid with NBPA, prepared by a process according to claim 1, 2, or 3.

* * * * *